United States Patent
Leske et al.

(10) Patent No.: US 8,249,267 B2
(45) Date of Patent: Aug. 21, 2012

(54) EARPHONE AND HEADSET

(75) Inventors: Olaf Leske, Langenhagen (DE); Olav Nisse, Hildesheim (DE)

(73) Assignee: Sennheiser electronic GmbH & Co. KG, Wedemark (DE)

( * ) Notice: Subject to any disclaimer, the term of this patent is extended or adjusted under 35 U.S.C. 154(b) by 656 days.

(21) Appl. No.: 12/493,653

(22) Filed: Jun. 29, 2009

(65) Prior Publication Data
US 2009/0323979 A1  Dec. 31, 2009

(30) Foreign Application Priority Data
Jun. 30, 2008 (DE) .......... 10 2008 031 017

(51) Int. Cl.
*A61F 11/06* (2006.01)
(52) U.S. Cl. .......... 381/72; 381/378
(58) Field of Classification Search .......... 381/72, 381/374, 376, 377, 378, 379, 383, 309, 370; 181/128, 129; 379/430
See application file for complete search history.

(56) References Cited

U.S. PATENT DOCUMENTS

| | | | |
|---|---|---|---|
| 1,546,567 A | 7/1925 | Childress | |
| 1,552,593 A | 9/1925 | Childress | |
| 1,649,551 A | 11/1927 | Smith | |
| 3,193,841 A | 7/1965 | Haluska | |
| 3,325,824 A | 6/1967 | Donegan | |
| 3,381,559 A | 5/1968 | Lefever et al. | |
| 3,447,160 A | 6/1969 | Teder | |
| 3,682,268 A | 8/1972 | Gorike | |
| 3,787,894 A | 1/1974 | Goodman, Jr. | |
| 4,259,747 A | 4/1981 | Taesler et al. | |
| 4,409,442 A * | 10/1983 | Kamimura | 381/383 |
| 4,571,746 A * | 2/1986 | Gorike | 2/209 |
| 4,783,822 A | 11/1988 | Toole et al. | |
| 5,293,647 A | 3/1994 | Mirmilshteyn et al. | |
| 6,333,982 B1 * | 12/2001 | Sapiejewski et al. | 379/430 |
| 6,385,325 B1 * | 5/2002 | Nageno et al. | 381/374 |
| 6,449,806 B1 * | 9/2002 | Engelhard et al. | 24/3.1 |
| 8,050,444 B2 * | 11/2011 | Smith | 381/379 |
| 2002/0025057 A1 * | 2/2002 | Bebenroth | 381/379 |
| 2009/0323978 A1 * | 12/2009 | Leske et al. | 381/72 |

FOREIGN PATENT DOCUMENTS

| | | |
|---|---|---|
| DE | 2132817 A | 1/1972 |
| DE | 3118294 C2 | 3/1982 |
| DE | 10310084 A1 | 9/2004 |
| EP | 1638364 A2 | 3/2006 |

* cited by examiner

*Primary Examiner* — Vivian Chin
*Assistant Examiner* — Friedrich W Fahnert
(74) *Attorney, Agent, or Firm* — Kilpatrick Townsend & Stockton LLP

(57) ABSTRACT

There is provided an earphone comprising a hoop band (1) for receiving at least one ear pad (OM). The hoop band (1) has at least two hoop band portions (2a, 2b), wherein at least two of the hoop band portions (2a, 2b) are rotatably connected together by way of a rotary joint unit (5). In addition in the region of the rotary joint unit the hoop band has a spring unit (10) which couples the two hoop band portions together and thus exerts a spring force on the hoop band portions (2a, 2b), wherein the spring force is adjustable by adaptation of the coupling by way of a coupling means.

8 Claims, 2 Drawing Sheets

EARPHONE AND HEADSET

CROSS-REFERENCE TO RELATED APPLICATIONS

This application claims priority to German Patent Application No. 10 2008 031 017.4, filed Jun. 30, 2008, the disclosure of which is hereby incorporated by reference in its entirety.

The present invention concerns an earphone, a headset and an ear protection.

BACKGROUND

Headphones and headsets in which the hoop band contact pressure force is adjustable have long been known. Hereinafter the term hoop band contact pressure force is used to denote that force with which the ear pads are pressed against the head when the headphones or headset is fitted. In typical configurations that force can be adjusted by the provision of a possible way of altering the geometry of the hoop band or the coupling between the hoop band and the ear pads.

U.S. Pat. No. 5,293,647 describes headphones in which a one-part head hoop band is coupled at both ends to a respective ear pad by way of two interconnected rotary joints. The connected rotary joints are respectively fixed by way of a common fixing plate which can be operated by way of a centrally mounted adjusting button with a traction spring. When the fixing plate is released for unlocking the rotary joints by way of the central adjusting button the position of the ear pads relative to the head hoop band can be altered. The described headphones thus permit a certain adjustability of the hoop band contact pressure force but it will be noted that they do not permit comfortable operation as a total of four rotary joints are to be adjusted jointly in regard to an overall effect.

U.S. Pat. No. 3,682,268 describes headphones having a head hoop band comprising a plurality of connected parts which are substantially in the form of hollow bodies. One or more springs integrated into the head hoop band produce a hoop band contact pressure force for pressing the ear pads against the head when the headphones are fitted. It will be noted however that the stress of the springs and therewith the hoop band contact pressure force cannot be varied in those headphones. In addition the described structure of the head hoop band in the form of hollow bodies results in markedly larger structural shapes than can be achieved with present day head hoop band forms.

SUMMARY

Therefore the object of the present invention is to provide an earphone, a headset and an ear protection which permit better adjustability of the hoop band contact pressure force.

Thus there is provided an earphone having a hoop band for receiving at least one ear pad. The hoop band has at least two hoop band portions, wherein at least two of the hoop band portions are rotatably connected together by way of a rotary joint unit. In the region of the rotary joint unit the hoop band further has a spring unit which couples the two hoop band portions together and thus exerts a spring force on the hoop band portions, wherein the spring force is adjustable by adaptation of the coupling by way of a coupling means.

The invention concerns the idea of providing an earphone in which at least a first and a second hoop band portion of a multi-part hoop band are rotatably connected together by way of a rotary joint unit. In the region of the rotary joint unit the hoop band has a spring unit having a spring axis which couples the hoop band portions together. The spring unit applies to the hoop band portions a spring force by which the ear pads are pressed against the head when the earphone is fitted.

In accordance with an aspect of the invention the spring unit is in the form of a torsion spring so disposed in the region of the rotary joint unit that the spring axis coincides with the axis of rotation. That permits a flat structure whereby integration into the hoop band is facilitated.

In accordance with a further aspect of the invention the torsion spring is fixedly connected at a first end to the first hoop portion and at a second end to a coupling means. The torsion spring can be coupled adjustably by way of the coupling means to a first end of the complementary second hoop band portion. The spring force acting on the hoop band portions and therewith the hoop band contact pressure force are adjustable by adjustment of the coupling.

In accordance with a further aspect of the invention the coupling means is in the form of a latching disk which is oriented substantially perpendicularly to the spring axis of the torsion spring and which has a number of latching projections. The first end of the second hoop band portion has corresponding latching grooves into which the latching projections are latchable for coupling the torsion spring to the second hoop band portion.

In accordance with still a further aspect of the invention the torsion spring can additionally be used as a compression spring. That applies to the latching disk a compression force acting substantially in the direction of the spring axis so that the latching projections latch into the corresponding latching grooves. In that way the torsion spring itself is operable to produce stable coupling to the second hoop band portion.

In accordance with a further aspect of the invention the first hoop band portion has an adjusting button. By actuation of the adjusting button, the latching disk can be pushed away against the compression force of the torsion spring to release the coupling to the second hoop band portion.

In accordance with still a further aspect of the invention the adjusting button is latchable on at least one of the latching projections of the latching disk. In that way the torsion spring is secured upon actuation of the adjusting button in such a way that the torsion spring force of the spring is not variable during actuation of the adjusting button. That aspect of the invention makes it possible to adjust the torsion spring force acting on the hoop band portions, and thus the hoop band contact pressure force, in a wide range of adjustment, as described hereinafter.

To increase the hoop band contact pressure force firstly the adjusting button is actuated whereby the coupling of the torsion spring to the second hoop band portion is released and the latching disk is secured by the adjusting button. Thereafter the first and second hoop band portions are moved downwardly towards each other and the adjusting button is released again. When now the first and second hoop band portions are moved upwardly again the torsion spring force of the torsion spring is increased by virtue of the existing coupling action to the two hoop band portions. The described tightening operation can be repeated one or more times to further increase the torsion spring force of the torsion spring.

The reverse movements are to be implemented to reduce the hoop band contact pressure force. The adjusting button is actuated to release the coupling of the torsion spring to the second hoop band portion and to secure the latching disk by the adjusting button. Thereupon the first and second hoop band portions are moved upwardly from each other and the adjusting button is released again. When now the first and second hoop band portions are moved downwardly again the torsion spring force of the torsion spring is reduced by virtue of the existing coupling effect to the two hoop band portions. Similarly to the tightening operation, in the operation of relieving the torsion spring the torsion spring force can be further reduced by repeating the above-described relief procedure a plurality of times.

BRIEF DESCRIPTION OF THE DRAWINGS

The advantages and embodiments by way of example of the invention are described in greater detail hereinafter with reference to the drawings.

DETAILED DESCRIPTION

Figure 1:
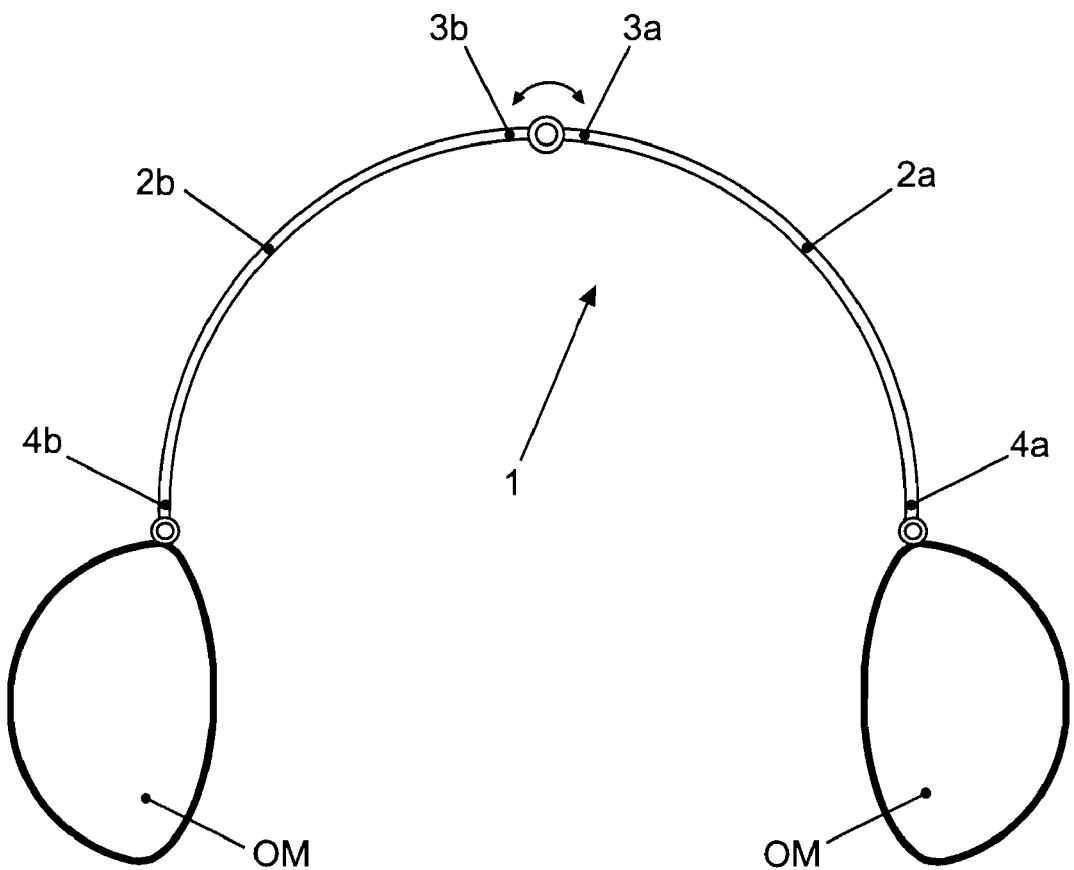
FIG. 1 shows a diagrammatic view of headphones in accordance with a first embodiment.

FIG. 1 shows a diagrammatic view of headphones in accordance with a first embodiment. The headphones have a hoop band 1 with a first hoop band portion 2a and a second hoop band portion 2b. A first end 3a of the first hoop band portion 2a is rotatably connected to a first end 3b of the second hoop band portion 2b. The two hoop band portions 2a and 2b involve a curvature along a common circular arc disposed in a first plane. The axis of rotation is oriented substantially perpendicularly to the first plane. Ear pads OM can be provided at a second end 4a of the first hoop band portion 2a and at a second end 4b of the second hoop band portion 2b.

Figure 2:
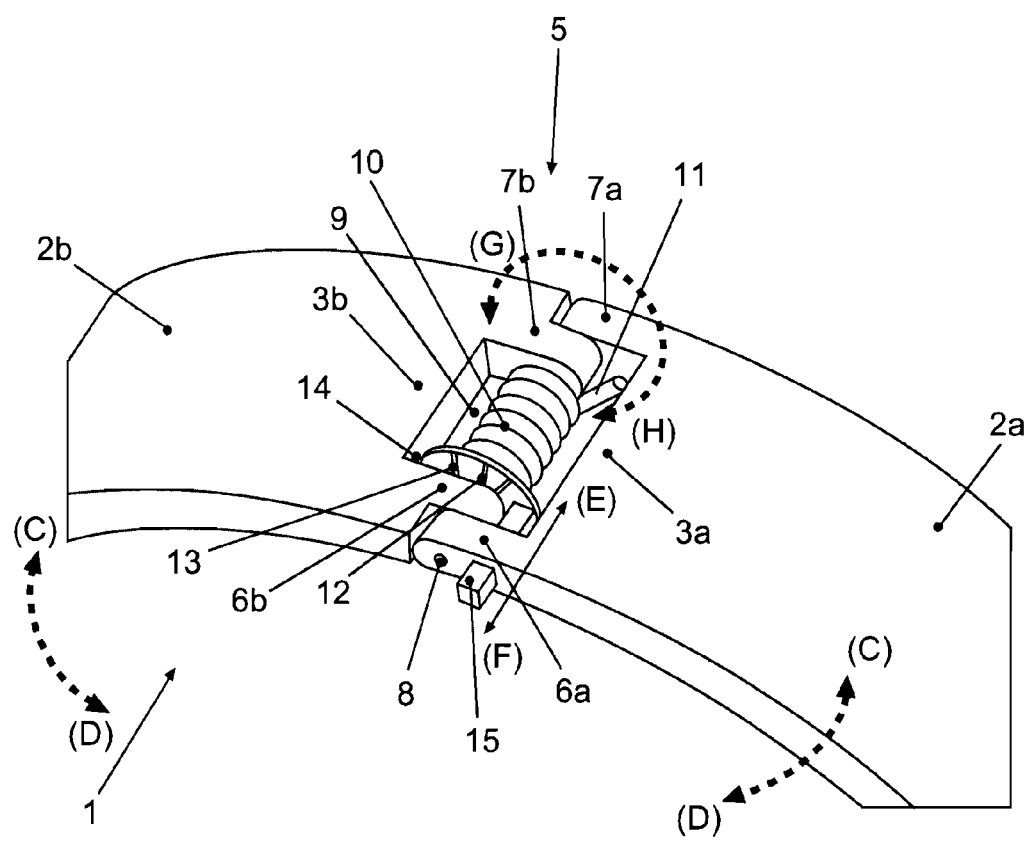
FIG. 2 shows a portion in detail of a perspective view of a headphones hoop band according to the first embodiment.

FIG. 2 shows a portion in detail from a perspective view of a headphones hoop band in accordance with the first embodiment. The connection of the first and second hoop band portions 2a and 2b has a rotary joint unit 5. The two hoop band portions 2a and 2b form two respective hinge joint limbs at the end parts of the respective first ends 3a and 3b respectively, wherein the two hinge joint limbs 6a and 7a of the first hoop band portion 2a are arranged further outwardly than the complementary hinge joint limbs 6b and 7b of the second hoop band portion 2b. The inner spacing of the two hinge joint limbs 6a and 7a is equal to the outer spacing of the two hinge joint limbs 6b and 7b so that the two hoop band portions 2a and 2b can be brought together in accurately fitting relationship in the rotary joint unit 5. The hinge joint limbs 6a, 7a, 6b, 7b have holes in the direction of the axis of rotation, by way of which holes they can be rotatably connected together with a hinge pin 8 passing therethrough.

Between the hinge joint limbs 6b and 7b the first end 3b of the second hoop band portion 2b has an opening 9 so that the hinge joint pin 8 passing therethrough is exposed in that region of the rotary joint unit 5.

In the opening 9, the rotary joint unit 5 has a spring unit, here a torsion spring 10, which is mounted on the hinge pin 8 rotatably and displaceably in the direction of the axis of rotation. The axis of the torsion spring 10 is coincident with the axis of rotation of the rotary joint unit 5. At its first end the torsion spring 10 has a spring limb 11 connected to the first hoop band portion 2a. At its second end the torsion spring 10 is connected to a coupling means, by way of which the torsion spring 10 can be coupled to the first hoop band portion 6a.

In accordance with the first embodiment the coupling means can be in the form of a latching disk 12 which is oriented substantially perpendicularly to the axis of the torsion spring 10 and which has a hole for the hinge pin 8 to pass therethrough. The latching disk 12 has two sides, an inside and an outside. The inside is (fixedly) to the second end of the torsion spring 10 while the outside has projections, hereinafter referred to as latching projections 13. In complementary relationship to the latching projections 13 on the latching disk 12 the first hinge joint limb 6b has at the first end 3b of the second hoop band portion 2b recesses which are referred to hereinafter as latching grooves 14.

The torsion spring 10 is designed in such a way that there is a certain spacing between the turns thereof so that the torsion spring 10 can additionally be used as a compression spring. The width of the opening 9 for installation of the torsion spring 10 and the latching disk 12 connected thereto is such that the torsion spring 10 exerts on the latching disk 12 a compression force D acting substantially in the direction of the spring axis, whereby the latching disk 12 is pressed against the first hinge joint limb 6b at the first end 3b of the second hoop band portion 2b. As the latching projections 13 on the latching disk 12 come into hooking engagement in the corresponding latching grooves 14 the torsion spring 10, in that condition, is releasably coupled to the second hoop band portion 2b by way of the latching disk 12 so that a torsion spring force T acts on the two hoop band portions 2a and 2b.

In accordance with the first embodiment the first hinge joint limb 6a at the first end 3a of the first hoop band portion 2a can have an adjusting button 15, by way of which the torsion spring force T acting on the two hoop band portions 2a and 2b is adjustable by adaptation of the coupling between the latching disk 12 and the first hinge joint limb 6b at the first end 3b of the second hoop band portion 2b.

When the adjusting button 15 is actuated it pushes the latching disk 12 inwardly against the compression force D of the torsion spring 10, acting substantially in the direction of the axis of the spring, whereby the coupling action between the latching disk 12 and the second hoop band portion 2b is released. In addition the adjusting button 15 latches on at least one of the latching projections 13 of the latching disk 12 whereby the latching disk 12 and therewith the torsion spring 10 are so secured that the torsion spring force T of the torsion spring 10 cannot be altered.

If now the first and second hoop band portions 2a and 2b are moved downwardly towards each other, then the angular position of the second hoop band portion 2b changes relative to the latching disk 12 as the torsion spring 10 connected to the first hoop band portion 2a and the latching disk 12 fixed by the adjusting button 15 are jointly rotated in the rotation of the first hoop band portion 2a about the axis of rotation of the rotary joint unit 5 and the second hoop band portion 2b is rotated in the direction of rotation opposite to the direction of rotation of the first hoop band portion 2a.

When the adjusting button 15 is no longer actuated then the latching disk 12 is pushed outwardly again by the compression force D of the torsion spring 10, acting substantially in the direction of the spring axis, and the latching projections 13 on the latching disk 12 come into hooking engagement in the latching grooves 14 of the second hoop band portion 2b so that the torsion spring 10 is coupled to the second hoop band portion 2b by way of the latching disk 12.

If the first and second hoop band portions 2a and 2b are moved upwardly again then the torsion spring force T of the torsion spring 10 is increased by virtue of the existing coupling action with the first and second hoop band portions 2a and 2b.

The described tightening operation can be repeated one or more times to further increase the torsion spring force T of the torsion spring 10.

The reverse movements are to be implemented to reduce the torsion spring force T of the torsion spring 10.

To release the coupling between the latching disk 12 and the second hoop band portion 2*b* the adjusting button 15 can be actuated so that it pushes the latching disk 12 inwardly against the compression force D of the torsion spring 10, acting substantially in the direction of the spring axis. In addition the adjusting button 15 latches on at least one of the latching projections 13 of the latching disk 12 whereby the latching disk 12 and therewith the torsion spring 10 are so fixed that the torsion spring force T of the spring is not variable.

If now the first and second hoop band portions 2*a* and 2*b* are moved upwardly away from each other then the angular position of the second hoop band portion 2*b* changes relative to the latching disk 12, similarly to the tightening operation.

When the adjusting button 15 is no longer actuated the latching disk 12 is pushed outwardly again by the compression force D of the torsion spring 10, acting substantially in the direction of the spring axis, and the latching projections 13 on the latching disk 12 hookingly engage into the latching grooves 14 of the second hoop band portion 2*b* so that the torsion spring 10 is coupled to the second hoop band portion 2*b* by way of the latching disk 12.

If the first and second hoop band portions 2*a* and 2*b* are moved downwardly again then the torsion spring force T of the torsion spring 10 is reduced by virtue of the existing coupling action to the first and second hoop band portions 2*a* and 2*b*.

Similarly to the tightening operation, in the procedure for relieving the torsion spring 10 the torsion spring force T can be further reduced by repeating the described relief procedure a plurality of times.

A second embodiment of the invention is based on the first embodiment, but in this case a headset is provided instead of an earphone. In that case a microphone is provided on the hoop band. The headset has at least one ear pad.

A third embodiment of the invention is based on the first embodiment, but here there is provided passive ear protection.

The invention claimed is:

1. An earphone comprising:
   a hoop band for receiving at least one ear pad, having at least a first and a second hoop band portion,
   a rotary joint unit for rotatably connecting the at least first and second hoop band portions, and
   a spring unit which has a spring axis and which couples the first and the second hoop band portions together in the region of the rotary joint unit and exerts a spring force on the first and second hoop band portions,
   wherein the spring force of the spring unit is adjustable.

2. An earphone as set forth in claim 1 wherein the spring unit has a torsion spring with a first and a second end, wherein the torsion spring is connected with the first end to the first hoop band portion and with the second end to a coupling means and wherein the torsion spring can be adjustably coupled to the second hoop band portion by way of the coupling means.

3. An earphone as set forth in claim 2 wherein the coupling means is in the form of a latching disk which is oriented substantially perpendicularly to the spring axis of the torsion spring and having a plurality of latching projections and wherein the second hoop band portion has a plurality of latching grooves into which the latching projections are latchable for coupling the torsion spring to the second hoop band portion.

4. An earphone as set forth in claim 3 wherein the torsion spring can additionally be used as a compression spring which exerts on the latching disk a compression force acting substantially in the direction of the spring axis so that the latching projections latch into the latching grooves.

5. An earphone as set forth in claim 4 wherein the first hoop band portion has an adjusting button for releasing the coupling by the latching disk being adapted to be pressed away against the compression force of the torsion spring.

6. An earphone as set forth in claim 5 wherein the adjusting button is latchable on at least one of the latching projections of the latching disk for fixing the torsion spring.

7. A headset comprising:
   a hoop band for receiving at least one ear pad, having at least a first and a second hoop band portion,
   a rotary joint unit for rotatably connecting the at least first and second hoop band portions, and
   a spring unit which has a spring axis and which couples the first and the second hoop band portions together in the region of the rotary joint unit and exerts a spring force on the first and second hoop band portions,
   wherein the spring force of the spring unit is adjustable.

8. An ear protection comprising:
   a hoop band for receiving at least one ear pad, having at least a first and a second hoop band portion,
   a rotary joint unit for rotatably connecting the at least first and second hoop band portions, and
   a spring unit which has a spring axis and which couples the first and the second hoop band portions together in the region of the rotary joint unit and exerts a spring force on the first and second hoop band portions,
   wherein the spring force of the spring unit is adjustable.

\* \* \* \* \*